(12) United States Patent
Smith

(10) Patent No.: US 7,763,293 B2
(45) Date of Patent: Jul. 27, 2010

(54) FISH FEED

(76) Inventor: Anthony George Smith, 105, Maes-Ty-Canol, Baglan, Port Talbot (GB) SA12 8UR ( * ) Notice: Subject to any disclaimer, the term of this patent is extended or adjusted under 35 U.S.C. 154(b) by 982 days.

(21) Appl. No.: 11/149,608

(22) Filed: Jun. 10, 2005

(65) Prior Publication Data

US 2006/0003049 A1    Jan. 5, 2006

Related U.S. Application Data

(63) Continuation-in-part of application No. PCT/GB03/05290, filed on Dec. 10, 2003.

(51) Int. Cl.
*A23K 1/18* (2006.01)
*A01K 67/033* (2006.01)

(52) U.S. Cl. .................. 426/2; 426/1; 426/89; 426/92; 426/98; 426/623; 426/635; 426/805

(58) Field of Classification Search .................. 426/89, 426/98, 630, 1, 805, 635, 2, 92, 623
See application file for complete search history.

(56) References Cited

U.S. PATENT DOCUMENTS 4,935,250 A * 6/1990 Cox .............................. 426/94
5,374,600 A   12/1994 Hozumi et al. .............. 502/402

FOREIGN PATENT DOCUMENTS

| GB | 2177588 A * | 1/1987 |
|----|-------------|--------|
| JP | 58187151 | 11/1983 |
| JP | 61202663 | 9/1986 |
| JP | 2-138943 | 5/1990 |
| JP | 02138943 | 5/1990 |
| JP | 07308138 | 11/1995 |
| KR | 2003073652 | 9/2003 |
| WO | WO98/44789 | 10/1998 |
| WO | WO02/00035 | 1/2002 |
| WO | WO02/24000 | 3/2002 |
| WO | WO 2004052118 A1 * | 6/2004 |

OTHER PUBLICATIONS

Dictionary meaning of "optimize" downloaded from http://www.merriam-webster.com/dictionary/optimize on Mar. 10, 2009.*
"Nutrient Requirements of Fish", National Research Council, pp. 49-54, 62-63, 1993.*
R. Metailler et al. "Weaning of Dover Sole (*Solea vulgaris*) Using Artificial Diets" J. World Maricol. Soc. 12(2):111-116 (1981).
Olive, P.J.W. et al. "Commercial production of polychaetes for angling: Implications for mainstream aquaculture" Aquaculture And The Environment, 1991, pp. 241-242, Special Publication, European Aquaculture Society, No. 14.
Fidalgo e Costa et al. "Growth, Survival and Fatty Acid Profile of Nereis Diversicolor (O.F. Muller, 1776) Fed on Six Different Diets" Bull. Mar. Sci. 67(1):337-343, 2000.
Whitfield et al. "Role of feed ingredients in the bromophenol content of cultured prawns" Food Chemistry 79 (2002) 355-365.

* cited by examiner

*Primary Examiner*—C. Sayala
(74) *Attorney, Agent, or Firm*—Waddey & Patterson, P.C.; Emily A. Shouse; Ryan D. Levy

(57) ABSTRACT

A fish feed comprising a plurality of pellets or particles, each pellet or particle having, as its principal component, a fresh cultured polychete product, together with at least one other naturally-occurring or organic material, so as to provide a composite diet comprising a balance of various nutrients as required by the aquatic creature for whom the feed is intended.

11 Claims, 1 Drawing Sheet

FISH FEED

CROSS-REFERENCES TO RELATED APPLICATIONS

This application is a Continuation-In-Part application which claims benefit of co-pending International Application PCT/GB2003/005290, with an international filing date of Dec. 10, 2003, entitled "Fish Feed" which is hereby incorporated by reference, Great Britain Patent Application No. 0228753.0 filed Dec. 10, 2002, which is hereby incorporated by reference, and Great Britain Patent Application No. 0312944.2 filed Jun. 5, 2003, which is hereby incorporated by reference.

STATEMENT REGARDING FEDERALLY SPONSORED RESEARCH OR DEVELOPMENT

Not Applicable

REFERENCE TO SEQUENCE LISTING OR COMPUTER PROGRAM LISTING APPENDIX

Not Applicable

BACKGROUND OF THE INVENTION

This invention relates to fish feed, and more particularly but not exclusively, to an improved composite fish feed for use in feeding cultured fish in aquatic farms and the like.

In any environment where fish or similar aquatic creatures are bred in captivity, it is obviously necessary to provide them with a balanced diet containing all of the nutrients which would be available to them in the wild, so as to ensure that healthy fish are reared.

There are many different types of feed available. For example, International Patent Application No. WO02/24000 describes feed pellets consisting of wheat, fish meal and maize gluten in various quantities. However, there are a number of issues to be considered in connection with fish feed of this type, including the sustainability of the ingredients, the provision of a balanced diet, and the preservation of the water quality over a period of time.

Polychetes have been used as part of a maturation diet for shrimp for over 15 years. These have generally been used fresh or fresh/frozen and have either been fed with other fresh or fresh/frozen materials such as Squid and Artemia or blended with dry materials immediately before feeding.

More recently polychetes have been used as part of a maturation diet for other species such as pelagic and demersal fish, being fed in a similar way to shrimp maturation diets. Polychetes represent an ingredient source that has extremely high levels of palatability as well as contributing a so-called "factor X" that brings species to sexual maturity.

International Patent Application WO02/00035 A1 describes a bioactive food complex product for use in aquaculture of shellfish and finfish. It is stated herein that aquaculture of shellfish and finfish provides high-value food products for human consumption and has been the most rapidly growing sector in international agribusiness. It is further stated that continued progress in aquaculture is limited by (a) the lack of adequate commercial feeds during critical hatchery and nursery phases, and (b) the devastating losses to disease in all production phases, particularly in shrimp farming. It goes on to say that hatchery and nursery operations typically depend on supplies of fresh and live food organisms, including polychete worms to produce aquaculture seedstock for grow-out and production aquafarms. However, because these foods are collected from the wild, they typically carry high bacterial loads. Thus, the use of fresh and live food organisms (collected from the wild) increases the risk of disease in the hatchery and these disease agents can be transported to nursery and grow-out facilities via the seedstock. This problem is addressed in WO02/00035 by providing a bioactive food complex including selected probiotics incorporated within the feed to assist in controlling bacterial diseases in aquaculture.

However, a further problem, which is not addressed in WO02/00035, is that the nutritional value of the wild, fresh food organisms which can be used in the type of bioactive food complex described is variable and is, in many cases, very low, depending on the environment from which they are collected. Some may, for example, have lived in an environment in which they were exposed to toxins; others may have had a shortage of nutritional sustenance. Thus, there is no consistency in the nutritional value of the resultant feed.

In summary there are a number of good reasons why fresh ingredients such as polychetes should be processed into Ready for Use feeds rather than taken to the hatchery as raw creatures, as listed below:
1. Variability in performance caused by Variability of Fresh Ingredients;
2. Variability in performance caused by poorly controlled blending/feeding;
3. Lack of Consistency of Supply;
4. Water Quality Problems;
5. Perceived or Real Risks of Spread of Disease;
6. Limitations to Use.

Looking at these issues in turn, if polychetes or other fresh materials are sourced by using indigenous supplies there can be variability in quality of the materials caused by poor control of harvesting. These wild caught materials are not controlled in a cultivated environment and are subject to seasonal, nutritional and life cycle changes. As an example small immature polychetes have a very different lipid profile to more mature animals. Wild caught animals are not likely to be put through a cleaning cycle at point of harvest to allow the intestine to empty and contamination with other species is likely, especially if for instance a dredging operation is used to catch them.

These same issues arise wherever a wild species is harvested without any attempt being made to control the cultivation of the species. Another and perhaps more serious issue is the potential for contamination of the fresh caught material from one of the many man-made toxins that we send down our rivers into the seas of the world. The potential issues with fishmeal are well known and these issues if anything can be more serious when harvesting estuarine creatures if the total environment they are growing in is not understood. Picture 2 shows a typical European beach from which wild polychetes are dug.

The answer to this is to sustain the population of the fresh ingredient by cultivation techniques, which for the marine polychete means growing the animal in land-based ponds, where careful control of feeding, water quality, time of harvesting and preparation between harvesting and processing are all able to be controlled carefully. With other fresh marine ingredient sources it is equally important to understand and control source of supply.

When putting together a typical shrimp maturation feed the operator is asked to take the fresh materials and chop them into a size suitable for feeding to the shrimp. Note that if the polychetes or other fresh ingredients are in frozen form they may contain a variable amount of moisture, depending on how they have been frozen. If they have been allowed to thaw or if unknown freeze/thaw cycles have occurred there may have been deterioration in the material before the operator gets hold if it.

The various fresh ingredients are chopped and fed in cycles, the uneaten remains being cleaned out of the tanks after a while. This gives the target species the opportunity to selectively feed, eating more of one of the fresh ingredients than the others. Use of only fresh ingredients also means there is no opportunity to supplement the feed with micro nutritional ingredients, thus limiting the end user in terms of feed formulation. Picture 4 of bag of frozen polychetes.

Finally, the end user depends when feeding fresh ingredients on a high level of skill at the point of feeding, the operator having to be consistent in the selection, preparation and feeding of the fresh ingredients. This is difficult enough when feeding species such as shrimp, but is even more difficult when maturing fish species and much more difficult with starter feed.

Currently, many fresh ingredients such as polychetes are harvested using an independent chain of individuals who supplement their income by going down to the beach and digging. This has resulted in apparently cheap costs for these materials, the cost being no more than the price a person expects for their labour. The real cost of this is now being realised, when the beaches that were the source of this abundant harvest are drying out. As in so many other areas where we harvest without replacement the earth is running out of yet another resource.

Feeding fresh materials can affect the quality of the water in the feeding tanks due to leaching from the feed into the water. Interstitial fluids from the fresh materials certainly leaches very quickly into the water where cells have been damaged during the cutting and preparation of the fresh materials for feeding. For this reason it is better if the fresh ingredients could be packaged in a way that would minimise leaching of these materials. Processing into an encapsulated, pelleted or flaked form can be carried out to achieve this.

If fresh ingredients are taken from the marine environment immediately adjacent to the fish or shrimp farms then fed back as maturation or brood stock feed there is a significant risk that any diseases will keep going round the loop, recontaminating new generations before they get anywhere near grow-out ponds or nets. In this circumstance there is a need to first carefully screen the wet ingredients for disease then, if necessary, ensure the fresh ingredients pass through a process which kills or inactivated the disease vector.

If the wet ingredients are taken from a location remote from the fish or shrimp farm the probability of disease transmission is reduced. If, to take it a stage further, the fresh ingredients come from a "cold water" northern climate and are used to feed "warm water" species in locations extremely remote from the source of the wet ingredients, the probability of disease transmission is almost eliminated. It is still important to monitor the fresh ingredients, pass them where necessary through a "heat break" or cycle designed to inactivate the disease, and carefully control growth and harvesting. When feeding sub-tropical shrimp a species such as the polychete *Nereis Virens* is a good candidate in that it grows in temperature latitudes only. An added security is if the wet ingredient, such as *Nereis Virens*, is farmed on land based ponds.

We have now devised an improved fish feed (which term is intended to include "bait" and the like), and method of producing same, in which at least some of the problems outlined above are at least alleviated.

BRIEF SUMMARY OF THE INVENTION

In accordance with a first aspect of the present invention, there is provided a method of producing a feed for aquatic creatures, the method comprising forming a composition having a balance of various nutrients required of a composite diet for said aquatic creatures by grinding or otherwise breaking down one or more fresh cultured polychetes and adding at least one naturally-produced or organic material thereto so as to form said composition, wherein the culture parameters during cultivation of said polychetes are controlled so as to optimise the occurrence of one or more of said nutrients in said cultured polychetes, the method further comprising a plurality of pellets or particles, including said composition.

The composition beneficially has said cultured polychetes as its principal component.

Also in accordance with the present invention, there is provided a feed produced in accordance with the method of the first aspect of the present invention.

In accordance with the second aspect of the present invention, there is provided a feed for aquatic creatures, especially fish, comprising a cultured polychete product and at least one carrier material, said carrier material being a naturally-produced product.

Also in accordance with the second aspect of the present invention, there is provided a method of producing a feed for aquatic creatures, especially fish, the method comprising the step of combining or mixing a cultured polychete product with at least one naturally-produced or organic carrier material.

The term "cultured" used herein is intended to mean "bred and/or reared in a controlled environment, such as a farm", as opposed to being caught in the wild.

It will be appreciated by a person skilled in the art that a polychete is any of a various annelid worms of the class Polychaeta, including mostly marine worms such as the lugworm, and characterised by fleshy paired appendages tipped with bristles on each body segment. However, the polychetes can be of marine or non-marine (i.e. freshwater or terrestrial) origin.

Thus, the present invention provides a feed for aquatic creatures which can be totally organic, entirely sustainable (cultured polychetes can be farmed in vast quantities, as required, under controlled conditions, which is obviously beneficial to the quality of the polychetes), provides a composite diet for fish and other aquatic creatures including a balance of various nutrients. Cultured polychetes are already known and widely used as brood stock maturation feed, but the whole worm is generally considered to be too large to feed young or newly-hatched fish (or fry).

As a result of the present invention, and as the polychete culture develops, the culture parameters can be manipulated so as to harvest the target species (polychetes, such as ragworms) at phases of optimal nutritional profiles. The cultured polychetes can be studied closely, and the resultant feeds tested, to identify further, specific feed-enhancing properties of various types of polychetes, which properties can be specifically promoted during polychete culture.

As the true nature of the polychete (say ragworm) culture is ecologically relatively friendly, the feed given to the ragworms can be carefully adjusted, relative to the commercial foods currently available, so as to incorporate various specialised ingredients, such as algaes, yeasts and brans, so as to enhance the above-mentioned properties of the polychetes. Such ingredients can be sourced from existing industries.

The method and feed of the present invention results in optimum feeds, and it has been shown by various recognised authorities in aquaculture that high densities using optimal feeds not only result in increased harvest biomass (and decrease in loss due to disease), but have the additional eco-friendly aspects of the provided facilities.

In one embodiment of the invention, the feed may comprise, in various quanitites, ground fresh cultured polychetes, at least one other natural food, such as mussel and/or oyster, and at least one carrier material such as wheat, or the like, which provides protein, bulks up the feed and helps to preserve the quality of the water in which the aquatic creatures live. However, it will be appreciated that there a number of different substances which could be added to the polychetes to provide the required characteristics. The main issue is the use of cultured polychetes used in their fresh, natural state (as opposed to dried and ground). The feed may be formed into pellets or particles of any of a variety of sizes, according to the size of the fish required to be fed therewith. It is, however, relatively important (although not essential) to provide pellets or particles of substantially equal size in a batch of feed.

There are many different processes which can be used to produce the feed of the present invention, most of which are known. For example, the ingredients can be mixed together, extruded, passed through a mesh or similar reticulated filter to create strands of a required thickness, and then passed through a spherizer which breaks the strands down into the required size of pellets or particles.

DETAILED DESCRIPTION OF THE INVENTION

Figure 1:
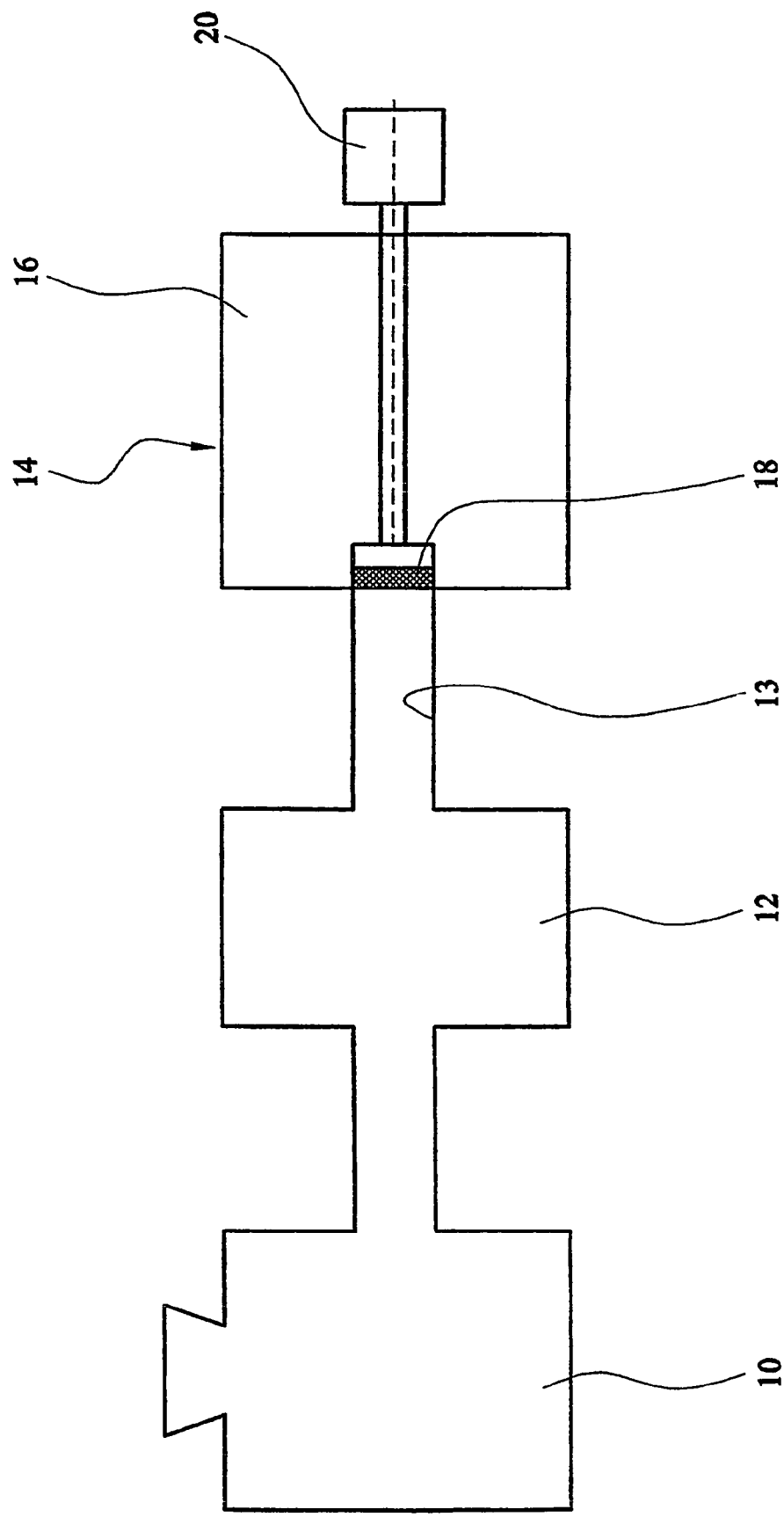
FIG. 1 is a schematic block diagram of apparatus suitable for use in making feed (or performing a method) according to an exemplary embodiment of the present invention.

An embodiment of the present invention will now be described by way of example only and with reference to the accompanying drawing, which is a schematic block diagram of apparatus suitable for use in making feed (or performing a method) according to an exemplary embodiment of the present invention.

In this exemplary embodiment of the invention, fresh, cultured polychetes are ground or otherwise broken down, and then mixed with ground mussel and/or oyster, and a carrier, such as wheat, which provides a good source of protein and helps to preserve water quality in the environment in which it is used. The mixture is passed to an extruder 10 which forces the mixture through a die to create long strands of the material. The strands are then passed through one or more meshes 12 or similar reticulated filter devices, to provide strands of any required thickness. The strands are then passed, via outlet 13, to a device 14 comprising a pellet chamber 16 having a rotating knife 18 arranged relative thereto with a drive 20, which is arranged to cut feed pellets into suitable lengths.

In an alternative embodiment, the mixture including fresh, cultivated polychetes can be used as a coating for feed pellets, formed of the above-mentioned composition or a different feed composition.

A number of different methods of processing the fish product, derived from the fresh, cultured polychetes, may be used, as will now be explained in more detail. However, it will be apparent to a person skilled in the art that the methods may also be available for use in this regard, and the invention is not intended to be limited in this respect.

Fishmeal is the traditional result of a fairly drastic way of processing a wet ingredient. The fish product (i.e. the fresh, cultured polychete) is dried and ground which creates a dry bulk solid that is relatively easy to handle and is stable for a long period of time at ambient temperatures. It would be possible to process all wet ingredients in this way but the essential downside to this, in some cases, is the loss of nutritive value. A classic problem in this field can be seen when spirulina is added as an ingredient to a dry extruded product, the spirulina losing part or all of its green colour in the extrusion process. Another example is the polychete worm that becomes flinty hard when heat processed on its own, making it extremely difficult to size reduce as a feed ingredient. There are many heat-sensitive nutrients in "wet" ingredients that may be denatured to a lesser or greater extent by high temperature and/or high shear processing and it is a further object of the invention to propose novel ways of processing these ingredients in ways that preserves to the maximum patatability and nutritional performance.

However, processing the wet ingredients by methods such as flaking or pelleting gives an opportunity to secure the product from disease risk, either by the nature of the process itself or by the use of upstream and downstream technologies to inactivate the target disease vector.

In any event, wet ingredients are being fed to adult stages of various species as a maturation diet and to larval and starter stages of many stages, in the form for instance of Artemia. For many wet ingredients, such as polychetes, squid, fresh fish, it is not possible to feed these to starter sizes because of the difficulties of size reduction to make the material suitable for the target species. This is where the wet material needs to be processed to bring it to a physical state which is suitable for delivery as a feed product.

Flaking technology is on the surface very simple, where one steam-filled drum at the same time both cooks and dries a batter slurry that is spread onto the surface of the drum. The slowly rotating drum gradually dries the film of batter slurry which leaves the drum after about three quarters of a revolution as a flake film.

The reality of course is that great care has to be taken with the formulation to create a slurry that will dry, cook and release from the drum. The flake is generally a starch-based formulation, the starch source having to be specially selected to create the required physical performance on the flaking drum.

Flake products are very popular and the process imparts virtually no mechanical shear and very little thermal heat damage to nutrients, if the process conditions are well balanced. A formulation can be made up with a very high level of wet ingredients and run successfully on a drum dryer, either to make a complete formulation or to create a specialised ingredient for further processing. The batter slurry stage of this process further creates an opportunity for some modification of ingredients by, for example, using enzymes to pre-digest ingredients in a controlled way, thus improving absorption of these ingredients.

Hot extrusion is the technology that most aqua-cultural feed companies are most familiar with. The extrusion cooker uses high levels of thermal and mechanical cook or work and then extrudes pellets through the terminal die system, the extrudate moisture content before exiting the die being typically 25%. This relatively low moisture content means that a relatively low proportion of "wet" ingredients can be used. If the pet food industry is observed it is possible to run at much higher extrudate moistures, but the corresponding pellet density increases, which may be a problem when try to make floating pellets! It can be observed in the pet food industry that the use of high levels of "wet" ingredients, usually meat, there is a differentiation between quality of products, the "superpremium" products being sold as nutritionally superior "high energy" products with a reduced and controlled "back end performance". This latter can be of some interest to aquaculturalists who are interested in maintaining water quality.

One serious issue with dry or hot extrusion is the damage done to nutrients in the extrusion process. This cannot be avoided in this type of process, but ways have been successfully investigated of overcoming this at the Dragon Feeds facility where a unique hot coating system has been developed to coat hot extruded pellets with a complex coating system that enhances palatability and carries heat sensitive micronutrients and colours.

Finally hot extrusion is used to make starter crumbles. These products tend to use very expensive ingredients and the crumbling process is inefficient, yields being as low as 40%. This, combined with the damage to nutrients in the hot extrusion process, is why cold extrusion may, in some cases be appropriate.

Cold extrusion is a process where the standard "hot" extruder cn be modified to mix the extrudate and squeeze it as a dough through a die which makes "noodles" or "spaghetti" strands of various sizes, depending on the final application. The strands are then passed onto a spinning disc "Sphereizing" TM machine, which converts the strands into pellets, the diameter of the pellets being the same as the diameter of the strands. The pellets have to be run at a higher moisture content than standard dry extruded pellets which means they have to be dried on an activated bed dryer. The cold extrusion process can extrude pellets down to 300 microns diameter which means that a fluidised bed type dryer is needed in any case. This machine can then also be used as a "pre-dryer" between the extruder/former and the standard existing plant dryer.

Because the product is run wetter from the extruder this means a higher level of "wet" ingredients can be used. If really high levels are to be incorporated there may need to be some pre-drying stage before this, such as drum drying or spray drying. Both are used successfully at Dragon Feeds facility, depending on product needs. The cold extrusion process is comparatively cold, maximum temperature leaving the extruder normally being no more than 60 degrees Celsius. The dryer, if well balanced, imparts minimum heat damage to ingredients which means that maximum nutritional value is obtained from high priced micro-ingredients.

Aquaculture pellets, whether they be a 100 micron agglomerate, a 500 micron cold extruded pellet or a 10 mm hot extruded pellet, all benefit from the use of an encapsulating coat. This can be used to apply heat sensitive ingredients and palatability enhancers to the outside of hot extruded pellets.

Encapsulation technology can also be applied to the outside of much smaller pellets, but more refined equipment may be needed. The product can be encapsulated in a spray dryer, on an agglomerating fluid bed dryer or in a dryer/coater, depending on particle size. There are structural materials present in polychetes and other wet ingredients that make them particularly suitable as an essential structural material in an encapsulating formula. This combined with the extremely high palatability performance of a polychete-coated product gives several advantages:

1. Enhanced Palatability;
2. Heat sensitive nutrients applied to outside of product;
3. Controlled leaching into water;
4. Improved float, where required;
5. Extended water life.

A specific embodiment of the present invention has been described above by way of example only, and it will be appreciated by a person skilled in the art that modifications and variations can be made to the described embodiment, without departing from the scope of the invention as defined in the appended claims. In particular, any suitable pelleting method or apparatus may be used. Furthermore, any suitable organic or naturally-produced materials may be added to the ground fresh polychete material to produce feeds according to the nutritional requirements of the creatures for whom they are intended.

What is claimed is:

1. A method of producing a feed for aquatic creatures, the method comprising forming a composition having a balance of various nutrients required of a composite diet for said aquatic creatures by grinding or otherwise breaking down one or more fresh cultured polychetes and adding a ground material chosen from oysters and mussels thereto so as to form said composition wherein the culture parameters during cultivation of said polychetes are controlled so as to optimise the occurrence of one or more of said nutrients in said cultured polychetes, the method further comprising providing said composition in the form of a plurality of pellets or particles, including said composition.

2. A method according to claim 1, including the step of adding a carrier material to the composition.

3. A method according to claim 2, wherein said carrier material comprises wheat.

4. A feed for aquatic creatures, comprising a cultured fresh polychete product and at least one carrier material, said carrier material being wheat, wherein the culture parameters during cultivation of the polychetes are controlled so as to optimize the occurrence of one or more of the nutrients in the cultured polychetes.

5. A feed according to claim 4, having said cultured fresh polychete product as its principal percentage component.

6. A feed according to claim 4, comprising a plurality of food particles or pellets coated with or encapsulated by a composition comprising at least said fresh, cultured polychete product and said carrier material.

7. A feed according to claim 4, further comprising additional material derived from a shellfish, selected from mussel and oyster.

8. A feed according to claim 4, consisting of a plurality of pellets or particles.

9. A method of producing a feed for aquatic creatures, the method comprising the steps of combining or mixing fresh, cultured polychete, or a product obtained therefrom with at least one material chosen from oysters and mussels to produce a composition, wherein the culture parameters of the polychetes are controlled during cultivation to optimize occurrence of one or more nutrients in the cultured polychetes.

10. A method according to claim 9, including the step of forming said composition into particles or pellets.

11. A method according to claim 10, including the step of encapsulating or coating food particles or pellets with said composition.

* * * * *